(12) United States Patent
Goncalvez De Almeida et al.

(10) Patent No.: US 8,148,592 B2
(45) Date of Patent: Apr. 3, 2012

(54) CATALYTIC TRANSALKYLATION OF DIALKYL BENZENES

(75) Inventors: José Luis Goncalvez De Almeida, Algeciras (ES); José Luis Berna Tejero, Boadilla del Monte (ES)

(73) Assignee: Cepsa Quimica, S.A., Madrid (ES)

( * ) Notice: Subject to any disclaimer, the term of this patent is extended or adjusted under 35 U.S.C. 154(b) by 364 days.

(21) Appl. No.: 12/299,871

(22) PCT Filed: May 8, 2006

(86) PCT No.: PCT/ES2006/000218
§ 371 (c)(1),
(2), (4) Date: Jul. 2, 2009

(87) PCT Pub. No.: WO2007/128842
PCT Pub. Date: Nov. 15, 2007

(65) Prior Publication Data
US 2010/0022814 A1    Jan. 28, 2010

(51) Int. Cl.
*C07C 6/12* (2006.01)
(52) U.S. Cl. .......................... 585/475; 585/474
(58) Field of Classification Search .................. 585/475, 585/474
See application file for complete search history.

(56) References Cited

U.S. PATENT DOCUMENTS

| | | | |
|---|---|---|---|
| 3,385,906 A | 5/1968 | Kaufman | |
| 3,751,504 A | 8/1973 | Keown et al. | |
| 4,016,218 A | 4/1977 | Haag et al. | |
| 4,169,111 A | 9/1979 | Wight | |
| 4,440,871 A | 4/1984 | Lok et al. | |
| 4,547,605 A | 10/1985 | Kresge et al. | |
| 4,599,470 A | 7/1986 | Gregory et al. | |
| 5,114,563 A | 5/1992 | Lok et al. | |
| 5,157,158 A | 10/1992 | Berna Tejero et al. | |
| 5,196,574 A | 3/1993 | Kocal | |
| 5,276,231 A | 1/1994 | Kocal et al. | |
| 5,902,917 A | 5/1999 | Collins et al. | |
| 5,959,168 A | 9/1999 | Van der Aalst et al. | |
| 6,096,935 A | 8/2000 | Schulz et al. | |
| 6,133,492 A | 10/2000 | Anantaneni | |
| 6,232,515 B1 | 5/2001 | Schulz et al. | |
| 6,888,037 B2 | 5/2005 | Dandekar et al. | |

FOREIGN PATENT DOCUMENTS

| | | |
|---|---|---|
| BR | 0204568 | 9/2004 |
| EP | 0 308 097 | 3/1989 |
| EP | 0 439 632 | 8/1991 |
| EP | 0 687 500 | 12/1995 |
| EP | 0 847 802 | 6/1998 |
| EP | 1 059 277 | 12/2000 |
| WO | WO 02/062734 A1 | 8/2002 |

OTHER PUBLICATIONS

Cavalli et al. "Iso-Branching of Linear Alkylbenzene Sulphonate (LAS), biodegradation study of two model compounds." *Toxicological & Environ. Chem. vol. 54.* 1996. pp. 167-186.

De Almedia et al. "Linear Alkylbenzene." *JAOCS. Vol. 71. No. 7.* 1994. pp. 675-693.

(Continued)

*Primary Examiner* — Thuan Dinh Dang
(74) *Attorney, Agent, or Firm* — Merchant & Gould P.C.

(57) ABSTRACT

The present invention relates to a method for performing catalytic transalkylation between long-chain dialkyl benzenes and benzene in order to obtain monoalkyl benzenes. As dialkyl benzene source, this method employs the by-products of a method for alkylation of benzene with linear $C_9$-$C_{16}$ monoolefins.

8 Claims, 2 Drawing Sheets

OTHER PUBLICATIONS

Da et al. "Liquid phase alkylation of toluene with 1-heptene over a HFAU zeolite: evidence for transalkylation between toluene and non-desorbed products." *Applied Catalysis A: General vol. 182.* 1999. pp. 407-411.

Heinze—Editor. *The CLER Review: Research Technology Public Policy. Vol. 2. No. 1* 1996. pp. 1-48.

Mavrodinova et al. "Transalkylation of toluene with cumene over zeolites Y Dealuminated in solid-state. Part I. Effect of the alteration of Broensted acidity." *Applied Catalysis A: General. Vol. 248.* 2003. pp. 181-196.

Meyers. *Handbook of Petroleum Refining Processes.* McGraw-Hill Book Company. 1986. pp. 1-1—1-22.

Meyers. *Handbook of Petroleum Refining Processes.* McGraw-Hill. 1997. pp. 2.55-2.62.

Ueda Y., "Aromatic hydrocarbon production process 2.Dealkylation, disproportionation, and transalkylation processes" *Petrotech Vol. 27. No. 3* 2004. pp. 244-248—English translation of abstract provided.

CATALYTIC TRANSALKYLATION OF DIALKYL BENZENES

This application is a National Stage Application of PCT/ES2006/000218, filed 8 May 2006 and which application is incorporated herein by reference. To the extent appropriate, a claim of priority is made to the above disclosed application.

FIELD OF THE INVENTION

The present invention relates generally to catalytic transalkylation reactions and particularly to smectite type catalysts.

STATE OF THE ART

Alkyl aromatic compounds are an important family of substances that are used as raw materials in many industrial fields, such as the field of plasticizers, polymeric materials, insecticides, in agriculture for preventing the agglomeration of fertilizers, in the manufacture of textiles and fabrics, in the leather and fur industry, herbicides, industrial cleaning processes, in the photography industry, in the manufacture of adhesives and in fire-fighting products such as wetting agents, in electrochemical processes for removing dirt and grease from the surface of a substrate, and in biodegradable detergents (*Surfactants in Consumers Products, Theory, Technology, and Application*, Edited by J. Falbe, Springer Verlag, 1987).

The usual process used by the petrochemical industry to produce alkyl aromatic compounds, especially for applications in detergents, consists of dehydrogenating linear paraffins to obtain linear monoolefins and then carry out the alkylation of benzene with said monoolefins. Linear alkyl benzene sulfonate (LAS) is produced by the sulfonation of linear alkyl benzene (LAB) and subsequent neutralization of the corresponding sulfonic acids (HLAS). The linear olefins used in this process have between nine and sixteen carbon atoms. The alkylation step occurs in liquid phase, on the presence of Friedel-Craft type catalysts, for example, hydrofluoric acid. The HF process is well known and commercially used, producing a high yield (>99% by weight) in LAB with a relatively low selectivity for the 2-phenyl isomer, lower than 20%. The integrated process for the production of LAB is described in the *Handbook of Petroleum Refining Process*, published by Robert A. Meyers, 1986, p. 1-23, incorporated herein as a reference. U.S. Pat. No. 5,276,231 describes the intermediate steps of the process for the production of LAB, such as the selective hydrogenation of the diolefin by-products formed in the dehydrogenation of paraffins and the removal of non-linear by-products from the stream of the dehydrogenation step. The use of HF has some drawbacks, because it requires careful handling and special equipment due to its corrosivity, which translates into an increase of the fixed and operating costs, therefore the development of alternative catalysts based on solids with an acid character has been attempted.

The prior art reports the use of many solid acid catalysts for the production of phenyl alkanes, such as synthetic faujasites (zeolites X and Y), zeolite L, ZSM-5, ZSM-18, ZSM-20, mordenite and offretite. The acidity of acid solids increases when they are fluorided, therefore their catalytic activity increases in processes for the alkylation of aromatic compounds, as proposed in U.S. Pat. No. 5,196,574, patenting a fluorided silica-alumina for the alkylation of benzene with olefins, and in U.S. Pat. No. 6,133,492, patenting the use a fluorided mordenite to carry out the same reaction. The zeolite solids mentioned herein are defined in the classification of the *Atlas of Zeolite Framework Types*, W. M. Meier, D. H. Olson and C. H. Baerlocher, 5$^{th}$ revised edition, 2001, Elsevier, which the present invention refers to.

Figure 1:
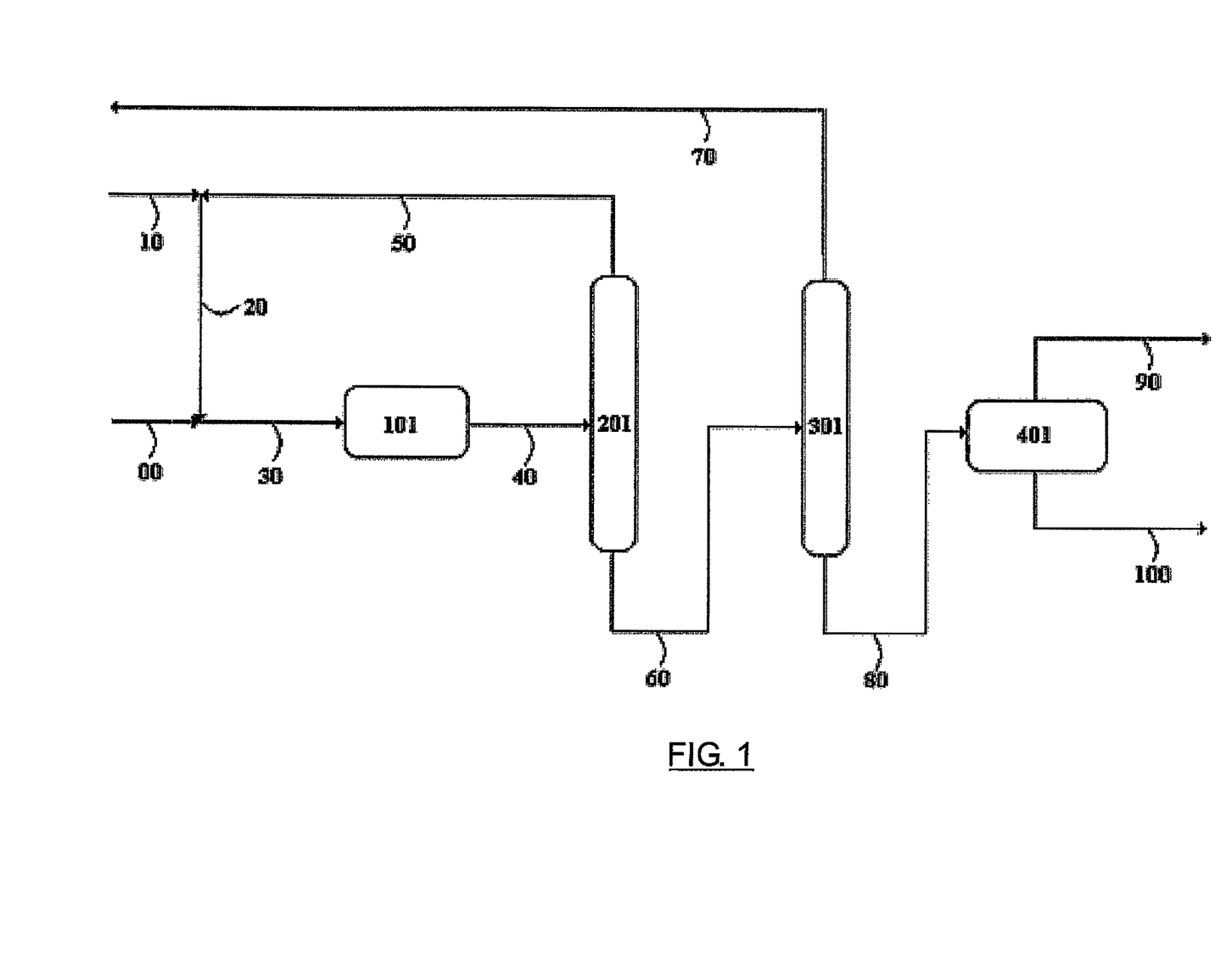
FIG. 1 shows the usual method for carrying out the fixed-bed alkylation in of benzene with $C_{10}$-$C_{13}$ olefins.

The usual method for carrying out the alkylation of benzene with $C_{10}$-$C_{13}$ olefins, as mentioned in the original references on fixed-bed (J. L. Berna Tejero, A. Moreno Danvila, U.S. Pat. No. 5,157,158, 1992; and J. L. G. De Almeida, M. Dufaux, Y. Ben Taarit and C. Naccache, *Journal of the American Oil Chemist's Society*, Vo. 71, No. 7, 675-694, 1994), is carried out in a process in which the alkylation step has a configuration as shown in a simplified manner in FIG. 1, showing how the monoolefin and paraffin mixture (stream 00) is mixed with benzene (stream 20) obtained upon mixing fresh benzene (stream 10) with recirculated benzene (stream 50) obtained in the benzene distillation column (201). The resulting reactive mixture (stream 30) is fed to the catalytic fixed-bed reactor (unit 101), in which the benzene is alkylated by the olefins. The reactor effluent (stream 40) formed by monoalkyl benzenes, unreacted benzene, paraffins and dialkyl benzenes, is fed to the benzene distillation column (unit 201), in which benzene is separated through the head and recirculated (stream 50). The bottom products (stream 60) are fed to the paraffin separation column (unit 301), in which the paraffins are separated through the head (stream 70) and recirculated to the dehydrogenation step.

The unit 301 bottom stream (stream 80), mainly formed by monoalkyl benzenes and dialkyl benzenes, is fed to the final purification unit (unit 401), in which the monoalkyl benzenes are separated from the heavier by-products by means of a distillation process and subsequently purified by means of a clay treater, thus obtaining a high-purity monoalkyl benzene stream (stream 90). The dialkyl benzenes and other heavy by-products leave the process through stream 100.

In this same sense, one of the main drawbacks associated to the alkylation process when linear olefins are used to produce alkyl benzenes in the detergent range is the generation of polyalkyl benzene compounds in the alkylation step. These unwanted by-products are generated due to the greater stability of their corresponding cationic intermediates provided by the +1 inductive effect of the alkyl chain. They can therefore be easily polyalkylated. This is the reason for which, in order to minimize unwanted polyalkylation reactions, the usual operating conditions on an industrial level involve high molar benzene to olefins ratios (above 3:1). But, although minimized, polyalkylation reactions take place, resulting in an inefficient use of the raw materials (a considerable fraction of benzene and olefins is "lost" in the form of dialkyl benzenes with low commercial value) and in high operating costs (due to the need to separate and recirculate large amounts of benzene). This is the reason for which a controlled transalkylation process would be desirable, because it would allow transforming dialkyl benzenes with little value into monoalkyl benzenes, which are much more commercially appreciated.

Isomerization and transalkylation are the two main reactions taking place when di or trialkyl benzenes are passed over solids based on silica-alumina or on metal-exchanged zeolites. The position isomerization of polyalkyl benzenes can be developed by means of two mechanisms: intramolecular 1,2 elimination and transalkylation. Isomerization through transalkylation predominates below 200° C., as described in *The Chemistry of Catalytic Hydrocarbon Conversions*, H. Pines, 1$^{st}$ Edition (1981), Academic Press. The state of the art in transalkylation/disproportionation and dealkylation processes has been summarized by Ueda Y., "*Aromatic hydrocarbon production process 2. Dealkylation, disproportionation, and transalkylation processes*", Petrotech 27/3 244-

248, (2004). These transalkylation processes have been widely studied for short-chain polyalkyl benzenes, such as xylene, cumene and associated trimethylbenzenes, polyethylbenzenes and polypropylbenzenes. The preparation of monoalkylated aromatic hydrocarbons through the transalkylation of polyalkylated aromatic hydrocarbons with aromatic substrates, in which zeolite catalysts with small, medium and large pores are used, is described in U.S. Pat. No. 3,385,906, U.S. Pat. No. 4,169,111 and EP 308,097. Other solid acid oxides used in the catalytic transalkylation of short-chain polyalkyl compounds are SAPOs and zirconium-based SAPOs modified with tungsten, as described in U.S. Pat. No. 5,114,563 and U.S. Pat. No. 4,440,871. Patents EP 439,632, EP 687,500, EP 847,802 and U.S. Pat. No. 5,902,917 propose the alkylation of benzene with ethylene or propylene and the transalkylation of diethylbenzene or diisopropylbenzene with benzene using zeolites Beta. The TA-4 zeolite catalyst is used in the Tatoray process (created by Toray Industries™ and developed and licensed by UOP™), in which the zeolites have two fundamental functions: the disproportionation of toluene to obtain benzene and xylene mixtures and also the transalkylation of trimethylbenzenes to obtain xylene mixtures (Jeanneret, J., Handbook of Petroleum Refining Processes. Myers R A., editor. New York: McGraw-Hill; 1997. p. 2.55.). Zeolite Y has been used in the transalkylation of toluene with cumene, as described in Mavrodinova V. et al, *Transalkylation of toluene with cumene over zeolites Y dealuminated in solid-state. Part 1. Effect of the alteration of Brönsted acidity*, Applied catalysis. A, General, 2003, 248 (1-2), 181-196. EP 1,059,277-A1 proposes the use of a zeolite Y for transalkylating polyethylbenzene to obtain ethylbenzene. Most of these processes are carried out in vapor phase. As regards the transalkylation of long-chain dialkyl benzenes, there is not much literature on suitable catalysts. Brazilian patent PI0200458-5 A proposes the transalkylation of long-chain polyalkyl benzenes with benzene, using solid acids such as zirconia modified with tungsten, sulfated zirconia, zeolites and $AlCl_3$ as catalysts.

Having analyzed the proposed catalysts for carrying out the transalkylation of short-chain polyaromatic compounds with aromatic molecules to obtain monoalkyl aromatic compounds, the usual configurations of the processes in which they are used are analyzed. When they are integrated in an alkylation process, the function of the transalkylation step is to increase the overall yield of the process towards monoalkyl aromatic compounds. As in the case of the catalysts, the state of the art in the field is focused on configurations for transalkylating short-chain polyalkyl aromatic compounds. In the case of the Mobil-Badger process with ethylbenzene in vapor phase, the transalkylation reaction takes place in the alkylation reactor by means of a double catalytic system or by means of a separate transalkylation reactor, as described in U.S. Pat. No. 3,751,504, U.S. Pat. No. 4,547,605 and U.S. Pat. No. 4,016,218. U.S. Pat. No. 5,902,917 and U.S. Pat. No. 6,096,935 describe processes for the transalkylation of alkyl aromatic compounds in which the feedstock is introduced in a transalkylation area and its effluent is then introduced in an alkylation step in the presence of an olefin alkylating agent. Another possibility consists of passing portions of the transalkylation effluent to a multistep alkylation reactor, as described in U.S. Pat. No. 6,232,515.

In order to clearly evaluate the benefits of the transalkylation process of the present invention, it is useful to define indices such as; conversion, selectivity for monoalkyl benzenes, homolog distribution and isomer distribution:

i) Fractional conversion in the transalkylation: In the transalkylation reaction considered in this patent, the aromatic compound (benzene) is always used in excess in relation to the stoichiometry of the transalkylation reaction (assuming a stoichiometric benzene to dialkyl benzenes ratio of 1:1). Fractional conversion can be defined as the fraction of limiting reactant that is consumed in the reaction to generate all the associated products:

$$Conversion = \frac{N_{A0} - N_A}{N_{A0}} \times 100$$

wherein $N_{A0}$ is the initial number of moles of the limiting reactant (dialkyl benzenes), and $N_A$ is the number of moles of these compounds at the reactor outlet.

ii) Selectivity for monoalkyl benzenes: It can defined as $$Sel_{monoalkyl\ benzene} = \frac{W_{monoalkyl\ benzene}}{W_{light} + W_{monoalkyl\ benzene} + W_{heavy\ alkylate}} * 100$$

Wherein $W_{monoalkyl\ benzene}$ is the mass of monoalkyl benzene produced, preferably in the $C_{10}$-phenyl to $C_{13}$-phenyl range, $W_{light}$ is the mass of all the generated compounds lighter than $C_{10}$-phenyl, and $W_{heavy\ alkylate}$ is the mass of all the generated compounds heavier than $C_{13}$-phenyl. The percentages by weight of said compounds can be used in an equivalent manner.

iii) Homolog distribution: The homolog distribution can be understood as the percentage by weight of each monoalkyl benzene homolog (same alkyl chain) produced. $C_9$-phenyl, $C_{10}$-phenyl, $C_{11}$-phenyl, $C_{12}$-phenyl ... up to $C_{16}$-phenyl can be distinguished.

iv) Isomer distribution: Among the monoalkylbenzenes produced, the isomer distribution can be defined as the percentage by weight of each type of isomer produced, such as 2-phenyl, 3-phenyl . . . 7-phenyl isomers, and also the branched alkylate.

linear 2-phenyl isomer (R = linear)

linear 3-phenyl isomer (R = linear)

linear 7-phenyl isomer (R = linear)

branched n-phenyl isomer
(branched R and/or R', n = 2-7)

The isomer distribution has an important role in the overall economic feasibility of the production process, in the quality of the end sulfonated product and also in its biodegradation rate. Two groups from these isomers are especially interesting when alkyl benzenes are used in detergent production. 2-phenyl isomers are the molecules in which the aromatic ring is bonded to the alkyl chain through the carbon in position 2 of said chain. LAB mixtures with external isomer (2/3-phenyl) contents greater than 60% provide, upon sulfonating and neutralizing, a LAS with greater detersive properties but which is very viscous, not very stable and has a low solubility.

Branched isomers are alkyl benzene molecules in which the alkyl chain is not linear. If there are non-terminal (internal, such as 5-methyl, 5-phenylalkane) quaternary carbons in said chains, the resulting alkyl benzene sulfonates show a lower biodegradation rate than linear sulfonates, as described in "Iso-branching of LAS biodegradation study of two model compounds", L. Cavalli, G. Cassani, M. Lazzarin, C. Maraschin, G. Nuzzi, J. L. Berna, J. Bravo, J. Ferrer, A. Moreno, *Toxicology & Environmental Chemistry*. Vol. 54, page 167-186, 1966 and "*Biodegradation of co-products of commercial LAS*", A. M. Nielsen, L. N. Britton, L. Cavalli, J. L. Berna, The Cler Review, Vol. 2, No. 1, page 14-27, 1996.

It can be observed that isomer distribution has an important role in the behavior of detergents derived from monoalkyl benzene sulfonates at the level of their detersive properties and also at an environmental level. As dialkyl benzenes are fundamentally formed by the dialkylation of benzene in the alkylation step, it would be desirable for the monoalkyl benzenes produced in the transalkylation step to maintain the same isomer distribution and molecular weight as the monoalkyl benzenes of interest in the alkylation step. Both groups of monoalkyl benzenes could thus be mixed without affecting any final property of the product, but considerably increasing the overall yield of monoalkyl benzenes of the process.

This invention relates to a process in which the transalkylation catalyst is very active, stable and selective for monoalkyl benzenes when it catalyzes the reaction between the dialkyl benzenes obtained as by-products of the alkylation step and benzene. Said monoalkyl benzenes can be mixed with the monoalkyl benzenes produced in the alkylation process in which the transalkylation would be integrated, thus increasing the overall yield of the process to monoalkyl benzenes.

There is therefore a need to find a method for obtaining monoalkyl benzenes with maximized detersive properties, with an optimal environmental behavior and in conditions of maximum efficiency in the use of the raw materials, and the manufacturing process of which has very low associated economic costs.

DESCRIPTION OF THE INVENTION

The present invention relates to a method for obtaining monoalkyl benzenes from polyalkyl benzenes by means of a catalytic transalkylation reaction, a smectite with modified acidity which is in solid state and has improved properties when transalkylating long alkyl chain polyalkyl benzenes with aromatic hydrocarbon to obtain monoalkyl benzenes is used as a catalyst, in such a way that the drawbacks described in the state of the art are overcome.

Thus, a first aspect of the present invention relates to a method for obtaining monoalkyl benzene compounds by means of catalytic transalkylation of polyalkyl aromatic compounds, comprising the following steps:
i) mixing polyalkyl aromatic hydrocarbons with aromatic hydrocarbons;
ii) catalytically transalkylating the mixture obtained in step i) in a transalkylation reactor comprising a catalyst;
iii) separating the product obtained in step ii) into a fraction comprising unreacted aromatic hydrocarbon, into a fraction comprising unreacted polyalkyl aromatic compounds and into a fraction comprising the generated monoalkyl aromatic compounds;
iv) mixing the polyalkyl aromatic compounds obtained in step iii) with fresh polyalkyl aromatic compounds;
v) recirculating the mixture obtained in step iv) to step i);
vi) mixing the aromatic hydrocarbons obtained in step iii) with fresh aromatic hydrocarbons; and
vii) recirculating the mixture obtained in step vi) to step i)

In a particular embodiment of the present invention, the polyalkyl aromatic hydrocarbons are dialkyl aromatic hydrocarbons, in a more particular embodiment they are dialkyl benzene hydrocarbons.

In one particular embodiment of the present invention, the aromatic hydrocarbon is benzene.

In a particular embodiment of the present invention, the alkyl chains present in the polyalkyl aromatic hydrocarbons contain between 5 and 20 carbon atoms, preferably between 9 and 16 carbon atoms.

In a particular embodiment of the present invention, the aromatic hydrocarbon and the polyalkyl aromatic hydrocarbon are mixed in a molar ratio comprised between 1:1 and 100:1, preferably 60:1.

In a particular embodiment, the catalyst of step ii) is arranged in the reactor in an arrangement selected from the group consisting of a fluidized bed, of a slurry reactor or of at least one catalytic fixed-bed.

In a particular embodiment of the present invention, the transalkylation reaction of step ii) is carried out in a reactor configuration comprising at least one of the reactor configurations selected from the group consisting of: an independent fixed-bed reactor, at least two fixed-bed reactors in parallel, at least two fixed-bed reactors in series and combinations thereof.

In a particular embodiment of the present invention, separation step iii) is carried out by means of selective decomposition and/or distillation of by-products and/or selective adsorption.

In a particular embodiment of the present invention, the catalyst present in step ii) is a smectite type catalyst with modified acidity.

In a particular embodiment, the catalyst of step ii) comprises:
  a) a total silicon:aluminium ratio between 2.0:1.0-10.0:1.0, preferably about 5.6:1.0
  b) between 0.5-4% by weight of magnesium, preferably 1.2%
  c) between 0.2-3% by weight of iron, preferably 0.9%
  d) between 0.1-2% by weight of calcium, preferably 0.4%
  e) between 0.1-2% by weight of sulfur, preferably 0.5%
  f) between 0.01-0.5% by weight of fluorine
  g) between 0.0001%-0.005% by weight of sodium.

In a particular embodiment of the present invention, the catalyst of step ii) comprises:
  a) an X-ray powder diffraction pattern, characterized in that the most intense diffraction peak appears at the 2 theta angle corresponding to 5.74° and the remaining main peaks appear at 2 theta diffraction angles corresponding to 19.77°-26.33°-54.11°-61.85°-68.11° and 76.33°
  b) a total specific area (BET) between 200 to 800 $m^2/g$, preferably about 390 $m^2/g$;
  c) a total pore volume between 0.1 to 1 ml/g, preferably 0.5 ml/g
  d) a distribution of macropores with a diameter between 20 to 2000 angstrom, preferably between 20 to 60 angstrom, more preferably 40 angstrom.

In a particular embodiment of the present invention, the acidity of the catalyst of step ii) has a total acid center concentration of 100 to 900 micromoles per gram, preferably between 130 to 400 micromoles per gram.

In a particular embodiment of the present invention, the optimal reaction temperature is comprised between 150-250° C., preferably between 180-225° C.

In a particular embodiment of the present invention, the optimal reaction pressure is comprised between 15-50 kgf/cm$^2$, preferably between 30-45 kgf/cm$^2$.

In a particular embodiment of the present invention, the optimal liquid hourly space velocity (LHSV) is comprised between 0.5-5 h$^{-1}$.

BRIEF DESCRIPTION OF THE DRAWINGS

The linear monoolefin and paraffin mixture (stream 00) is mixed with benzene (stream 20) obtained upon mixing fresh benzene (stream 10) with recirculated benzene (stream 50) obtained in the benzene distillation column (stream 201). The resulting reactive mixture (stream 30) is fed to the catalytic fixed-bed reactor (unit 101), in which the benzene is alkylated by the olefins. The reactor effluent (stream 40) formed by monoalkyl benzenes, unreacted benzene, paraffins and dialkyl benzenes, is fed to the benzene distillation column (unit 201), in which benzene is separated through the head and recirculated (stream 50). The bottom products (stream 60) are fed to the paraffin separation column (unit 301), in which the paraffins are separated through the head (stream 70) and recirculated to the dehydrogenation step. The unit 301 bottom stream (stream 80), mainly formed by monoalkyl benzenes and dialkyl benzenes, is fed to the final purification unit (unit 401), in which the monoalkyl benzenes are separated from the heavier by-products by means of a distillation process and subsequently purified by means of a clay treater, thus obtaining a high-purity monoalkyl benzene stream (stream 90). The dialkyl benzenes and other heavy by-products leave the process through stream 100.

DETAILED DESCRIPTION OF THE INVENTION

Figure 2:
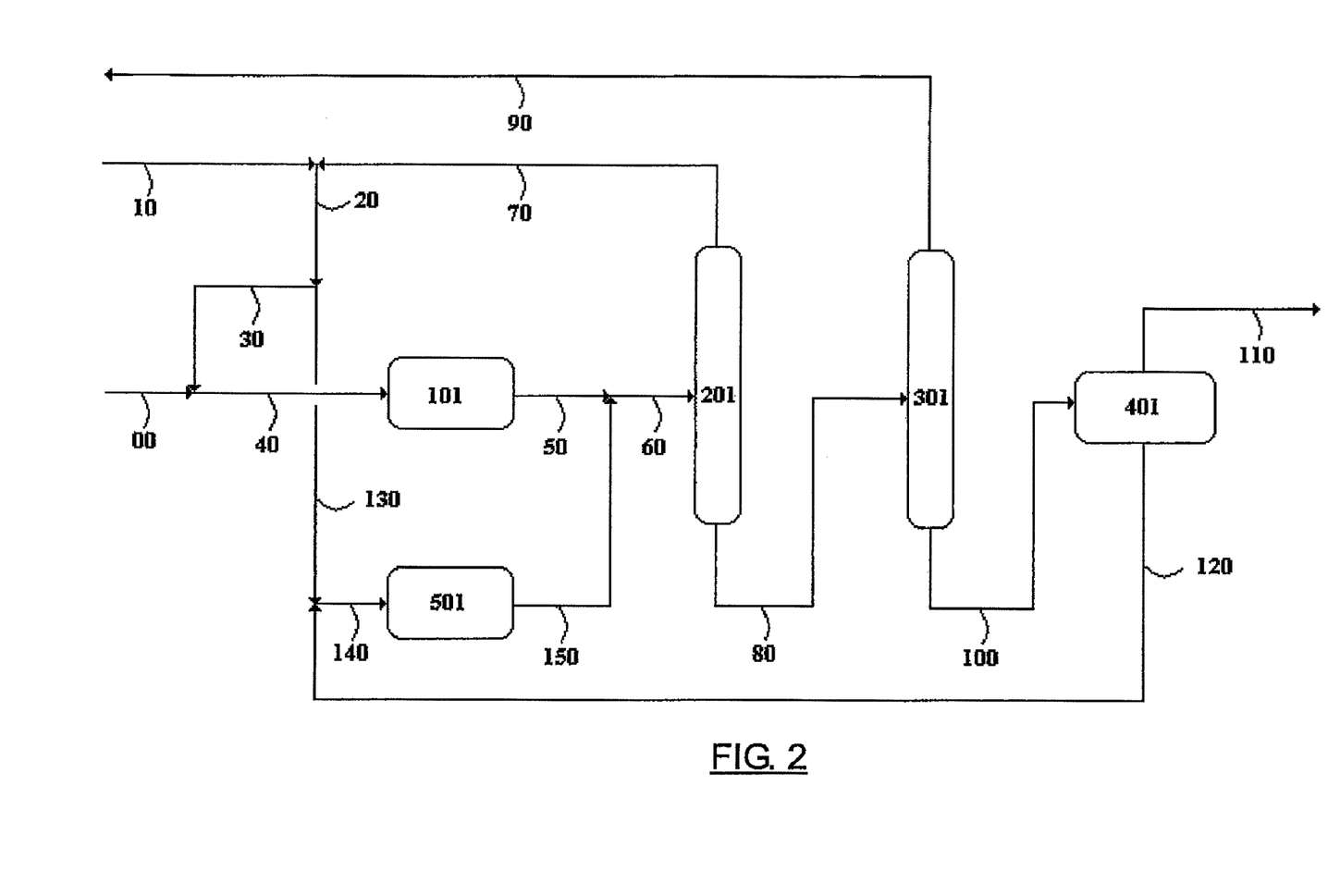
FIG. 2 shows a diagram of the reaction of the present invention in the form of a flow diagram.

FIG. 2 shows a non-limiting diagram for implementing this invention.

The linear monoolefin and paraffin mixture of the dehydrogenation, diolefin conversion and purification steps (stream 00) is mixed with a suitable amount of benzene (stream 30), obtained upon taking part of the benzene stream (stream 20) generated upon mixing fresh benzene (stream 10) with recirculation benzene (stream 70). The resulting reactant mixture (stream 40) is fed to the fixed-bed alkylation reactor (unit 101), in which the benzene is alkylated by the olefins. The alkylation effluent (stream 50), formed by monoalkyl benzenes, unreacted benzene, paraffins and dialkyl benzenes, is mixed with the effluent (stream 150) of the transalkylation reaction (unit 501), generating a stream (stream 60) formed by monoalkyl benzenes, unreacted benzene, paraffins and dialkyl benzenes that have not reacted in the transalkylation reaction, plus those formed in the alkylation reaction (unit 101). The stream 60 is fed to the benzene distillation column (unit 201), in which benzene is separated through the column head and is recirculated (stream 70) in order to the mixed with the fresh benzene supply (stream 10). The benzene column bottom stream (stream 80) is fed to the paraffin distillation column (unit 301), in which the paraffins are separated through the head and recirculated (stream 90) to the dehydrogenation unit of the alkylation process. The bottom of unit 301, which is fundamentally formed by monoalkyl benzenes and dialkyl benzenes (stream 100), is fed to the final purification step (unit 401), in which the monoalkyl benzenes are separated from the heavy by-products forming the dialkyl benzenes by means of a distillation step, followed by a purification with a clay bed, thus obtaining high-purity monoalkyl benzenes (stream 110). The by-products obtained in the purification of the monoalkyl benzenes are fundamentally dialkyl benzenes emerging from the purification unit 401 through stream 120. This stream is mixed with a benzene stream (stream 130), thus generating a benzene and dialkyl benzene mixture with a suitable molar ratio (stream 140). This stream is fed to the transalkylation reactor (unit 501), in which the transalkylation reaction takes place, The transalkylation effluent (stream 150) is sent to a purification step (unit 201) together with the alkylation reactor effluent, in which the unreacted benzene is recovered. The space velocity of the transalkylation step is controlled in order to be able to transform the dialkyl benzenes generated in the alkylation step.

The invention is additionally described, for illustrative purposes only, through the following examples which should never be considered as limiting the scope of the present invention.

EXAMPLES

Example 1

This example shows the behavior of the selected catalyst when it is used in the transalkylation of long-chain dialkyl benzenes with benzene to produce the corresponding monoalkyl benzenes. The selected catalyst has a smectite with modified acidity as a base. The reaction is carried out in a stainless steel reactor on a pilot plant scale, in which the catalyst was arranged in a fixed-bed. The dialkyl benzenes, which contained a minimum amount of monoalkyl benzenes, came from a benzene alkylation process with linear olefins in the $C_{10}$-$C_{13}$ range which used an acid solid as catalyst. These dialkyl benzenes were mixed with dry benzene until achieving a suitable molar benzene/dialkyl benzenes ratio. The percentage by weight of dialkyl benzenes and monoalkyl benzenes in the feed prior to the mixing with benzene is detailed in Table 1:

TABLE 1

| Component | % by weight in initial feedstock |
| --- | --- |
| Dialkyl benzenes | 96.3 |
| Monoalkyl benzenes | 3.7 |

The homolog distribution in the dialkyl benzenes used as feedstock is summarized in Table 2. As the dialkyl benzenes came from a benzene alkylation process with linear olefins in the $C_{10}$-$C_{13}$ range, said dialkyl benzenes had a carbon atom content comprised in the range between $C_{26}$ (didecylbenzene) and $C_{32}$ (ditridecylbenzene), because all the combinations between alkyl chains are possible. Furthermore, there are lighter dialkyl benzenes (<$C_{26}$) coming from the alkylation of short-chain alkyl benzenes generated in the dehydrogenation step with $C_{10}$-$C_{13}$ monoolefins, as well as heavier dialkyl benzenes (>$C_{32}$), generated by transalkylation processes occurring in the alkylation step:

TABLE 2

| Dialkyl benzene homologs (carbon range) | % by weight of each homolog in the dialkyl benzene mixture |
|---|---|
| <$C_{26}$ | 6.3 |
| $C_{26}$ | 4.3 |
| $C_{27}$ | 14.7 |
| $C_{28}$ | 26.2 |
| $C_{29}$ | 26.0 |
| $C_{30}$ | 15.0 |
| $C_{31}$ | 5.3 |
| $C_{32}$ | 2.0 |
| >$C_{32}$ | 0.2 |

Once mixed with benzene, the resulting dialkyl benzene and benzene mixture was heated until the suitable temperature and was then fed to the transalkylation reactor at a suitable liquid space velocity (LHSV), pressure and molar ratio of the reactants. Each transalkylation cycle involved 24 hours of reaction, followed by a 24 hour washing cycle with benzene. The operating conditions of both the reaction and the washing step are summarized in Table 3:

TABLE 3

| Catalyst bed volume (cm³) | 2000 |
|---|---|
| Reaction bed temperature (° C.) | 190-205 |
| Reaction pressure (kgf/cm²) | 39 |
| Reaction LHSV (h⁻¹) | 2 |
| Reaction time (h) | 24 |
| Bed temperature in washing step (° C.) | 230 |
| Washing pressure (kgf/cm²) | 39 |
| Washing LHSV (h⁻¹) | 6 |
| Washing time (h) | 24 |
| Molar benzene/dialkyl benzene ratio in reaction | 56 |

The operating temperature has been selected around 200° C. in order to optimize, from the energy point of view, the transalkylation process when it was integrated in a greater alkylation process. As commented above, in an alkylation process, the dialkyl benzenes come from a separation step based on a sequential distillation process. Distillation columns operate at bottom temperatures of the order of 200° C., therefore, considering that the feedstock of the transalkylation unit partly comes from these columns and that the transalkylation effluent will be separated in this distillation system, it would be interesting for its temperature to be slightly lower than said 200° C. to prevent intermediate heating/cooling steps before it is introduced in the columns, as the associated energy costs are thus minimized.

Four reaction cycles (each cycle being followed by its corresponding washing cycle) have been carried out, changing the reaction temperature. The results, expressed in terms of average dialkyl benzene conversion in each cycle, are summarized in Table 4:

TABLE 4

| Cycle | Reaction temperature (° C.) | Average dialkyl benzene conversion (%) |
|---|---|---|
| 1° | 190 | 70 |
| 2° | 195 | 71 |
| 3° | 200 | 72 |
| 4° | 205 | 73 |

As can be seen in Table 4, the average dialkyl benzene conversion increases slightly when the temperature increases. As has been considered above, a temperature slightly lower than 200° C. is preferable, therefore the temperature 195° C. has been selected to analyze the distribution of the reaction products shown below. The average composition at the indicated temperature of the transalkylation products and its comparison with the feedstock is summarized in Table 5:

TABLE 5

| Group of compounds | Average % by weight in feedstock | Average % by weight in effluent |
|---|---|---|
| By-products lighter than $C_{10}$-phenyl | 0.0 | 2.7 |
| Monoalkyl benzenes | 3.7 | 69.4 |
| Dialkyl benzenes | 96.3 | 27.9 |

The average composition corresponding to the effluent generated at 195° C. in terms of monoalkyl benzene homolog distribution and average molecular weight is summarized in table 6. Table 6 also incorporates the typical industrial specifications of the monoalkyl benzenes produced in an alkylation process (in terms of homolog distribution) in which this transalkylation process would be integrated, in order to see if both types of monoalkyl benzenes (those produced in the alkylation step and those generated in the transalkylation step) are similar:

TABLE 6

| | | Transalkylation effluent | Industrial specifications |
|---|---|---|---|
| Homolog series (% by weight over total monoalkyl benzenes) | Lighter than $C_{10}$-phenyl | 2.7 | <2 |
| | $C_{10}$-phenyl | 19.4 | <25 |
| | $C_{11}$-phenyl | 42.3 | >30 |
| | $C_{12}$-phenyl | 31.3 | >25 |
| | $C_{13}$-phenyl | 4.3 | <13 |
| | Heavier than $C_{13}$-phenyl | 0.0 | <2 |
| Average molecular weight (g/mol) | | 234 | 233-237 |

Other parameters that must be considered when analyzing the quality of the monoalkyl benzenes produced in the transalkylation process are the 2-phenyl isomer content (it conditions the final surfactant behavior of the product, as well as its biodegradability) and the amount of branched alkylate produced (it affects the final biodegradability of the product). Table 7 shows said parameters, corresponding to both the feedstock and to the effluent of the transalkylation reaction and to the usual industrial specifications relating to the linear monoalkyl benzenes of the $C_{10}$-phenyl to $C_{13}$-phenyl range which would be obtained in the alkylation process in which the transalkylation unit object of this patent would be integrated:

TABLE 7

| | Transalkylation feedstock | Transalkylation effluent | Industrial specifications |
|---|---|---|---|
| 2-phenyl isomer (% by weight over total monoalkyl benzenes) | 63.7 | 29.7 | 27-31 |
| Branched alkylate (% by weight over total monoalkyl benzenes) | 18.6 | 12.5 | <10 |

When Tables 5, 6 and 7 are analyzed, it can be seen that the monoalkyl benzenes produced by means of the transalkylation of dialkyl benzenes with benzene are almost identical, in terms of their most representative parameters, to the monoalkyl benzenes produced in the alkylation process from which the dialkyl benzenes used come. Only their light by-product (lighter than the $C_{10}$-phenyl) and branched monoalkyl benzene content (even though the latter are reduced to a great extent in comparison to the feedstock) is slightly higher than that of the desired monoalkyl benzenes. However, as the production of dialkyl benzenes in a benzene alkylation process with linear $C_{10}$-$C_{13}$ monoolefins involves about 5% of the total production, the mixtures of both monoalkyl benzenes meet the required industrial specifications.

Example 2

This example shows the stability over time of the activity of the catalyst used in the claimed transalkylation process, which is a fundamental parameter when considering its industrial application. The same reactor, feedstock mixture and operating conditions as in Example 1 have been used. The reaction temperature has been changed in the 185° C. to 200° C. range. 42 reaction cycles (each cycle being followed by its corresponding washing cycle) have been carried out to analyze the potential deactivation of the catalyst. Most of the reaction cycles developed lasted 24 hours, but some 48 hour cycles were also carried out. Table 8 shows the average dialkyl benzene conversion obtained during groups of cycles equivalent in reaction temperature and time (referred to as sequences) compared to the temperature of each sequence:

TABLE 8

| Sequence of cycles | Number of cycles in the sequence | Duration of each cycle (h) | Average sequence temperature (° C.) | Average dialkyl benzene conversion (%) |
| --- | --- | --- | --- | --- |
| 1 | 6 | 24 | 190 | 70 |
| 2 | 5 | 24 | 195 | 71 |
| 3 | 1 | 48 | 185 | 56 |
| 4 | 9 | 24 | 195 | 61 |
| 5 | 6 | 24 | 190 | 53 |
| 6 | 3 | 48 | 190 | 50 |
| 7 | 9 | 24 | 195 | 53 |
| 8 | 3 | 48 | 200 | 51 |

As can be seen in Table 8, the reaction system shows a high activity during the first eleven cycles (sequence 1), providing an average dialkyl benzene conversion of 70%. When the reaction cycle is extended to 48 hours (sequence 3), a decrease in the activity is observed, probably due to the fouling of the catalyst. A stabilization of the activity is then observed at about 51-52% of average conversion, regardless of the cycle temperature and duration. It seems to mean a stabilization of the catalyst. Therefore, this catalyst provides a stable process showing considerable heat tolerance and which even allows operating in 48 hour reaction cycles.

The invention claimed is:

1. A method for obtaining monoalkyl benzene compounds with an alkyl chain having a size of $C_{10}$ to $C_{20}$ by means of the catalytic transalkylation of dialkyl benzene compounds the alkyl chains of which have a size of $C_{10}$ to $C_{20}$, comprising the following steps:
   i) mixing dialkyl benzene compounds the alkyl chains of which have a size of $C_{10}$ to $C_{20}$ with benzene;
   ii) reacting the mixture of dialkyl benzene compounds with alkyl chains having a size of $C_{10}$ to $C_{20}$ and benzene obtained in step i) in a transalkylation reactor comprising a smectite type catalyst with modified acidity comprising;
   a) an X-ray powder diffraction pattern, characterized in that the most intense diffraction peak appears at the 2 theta angle corresponding to 5.74° and the remaining main peaks, ordered from greatest to lowest intensity, appear at 2 theta diffraction angles corresponding to 19.77°-26.33°-54.11°-61.85°-68.11° and 76.33°;
   b) a total acidity of acid centers of 100 to 900 micromoles per gram,
   c) a total specific area (BET) between 200 to 800 m²/g;
   d) a total pore volume between 0.1 to 1 ml/g;
   e) a distribution of macropores with a diameter comprised between 20 and 2000 angstrom;
   f) a total silicon:aluminium ratio between 2.0:1.0-10.0:1.0;
   g) between 0.5-4% by weight of magnesium;
   h) between 0.2-3% by weight of iron;
   i) between 0.1-2% by weight of calcium:
   j) between 0.1-2% by weight of sulfur;
   k) between 0.01-0.5% by weight of fluorine; and
   l) between 0.0001-0.005% by weight of sodium,
   iii) separating the product obtained in step ii) into a first fraction comprising unreacted benzene, into a second fraction comprising unreacted dialkyl benzene compounds with alkyl chains having a size of $C_{10}$ to $C_{20}$ and into a third fraction comprising the monoalkyl benzene compounds with an alkyl chain having a size of $C_{10}$ to $C_{20}$ generated in the catalytic transalkylation reaction of the dialkyl benzene compounds with $C_{10}$ to $C_{20}$ alkyl chains with benzene;
   iv) mixing the fraction comprising the unreacted dialkyl benzene compounds with alkyl chains having a size of $C_{10}$ to $C_{20}$ obtained in step iii) with fresh polyalkyl aromatic compounds;
   v) recirculating the mixture obtained in step iv) to step i);
   vi) mixing the unreacted benzene obtained in step iii) with fresh benzene; and
   vii) recirculating the mixture of unreacted benzene and fresh benzene obtained in step vi) to step i).

2. A method for obtaining mono alkyl benzene compounds with an alkyl chain having a size of $C_{10}$ to $C_{20}$ by means of the catalytic transalkylation of dialkyl benzene compounds the alkyl chains of which have a size of $C_{10}$ to $C_{20}$ with benzene according to claim 1, wherein benzene and the dialkyl benzene compounds the alkyl chains of which have a size of $C_{10}$ to $C_{20}$ are in a molar benzene:dialkyl benzene compounds ratio comprised between 1:1 and 100:1.

3. A method for obtaining mono alkyl benzene compounds with an alkyl chain having a size of $C_{10}$ to $C_{20}$ by means of the catalytic transalkylation of dialkyl benzene compounds the alkyl chains of which have a size of $C_{10}$ to $C_{20}$ with benzene according to claim 1, wherein the catalyst of the step ii) is arranged in the reactor in an arrangement selected from the group consisting of a fluidized bed, of a slurry reactor or of at least one catalytic fixed-bed.

4. A method for obtaining mono alkyl benzene compounds with an alkyl chain having a size of $C_{10}$ to $C_{20}$ by means of the catalytic transalkylation of dialkyl benzene compounds the alkyl chains of which have a size of $C_{10}$ to $C_{20}$ with benzene according to claim 1, wherein the transalkylation reaction of step ii) is carried out in a reactor configuration comprising at least one of the reactor configurations selected from the group consisting of: an independent fixed-bed reactor, at least two fixed-bed reactors in parallel, at least two fixed-bed reactors in series and combinations thereof.

5. A method for obtaining mono alkyl benzene compounds with an alkyl chain having a size of $C_{10}$ to $C_{20}$ by means of the catalytic transalkylation of dialkyl benzene compounds the alkyl chains of which have a size of $C_{10}$ to $C_{20}$ with benzene according to claim 1, wherein the separation step iii) is carried out by means of selective decomposition and/or distillation of by-products and/or selective adsorption.

6. A method for obtaining mono alkyl benzene compounds with an alkyl chain having a size of $C_{10}$ to $C_{20}$ by means of the catalytic transalkylation of dialkyl benzene compounds the alkyl chains of which have a size of $C_{10}$ to $C_{20}$ with benzene according to claim 1, wherein the optimal temperature for carrying out the transalkylation reaction is comprised between 150-250° C.

7. A method for obtaining mono alkyl benzene compounds with an alkyl chain having a size of $C_{10}$ to $C_{20}$ by means of the catalytic transalkylation of dialkyl benzene compounds the alkyl chains of which have a size of $C_{10}$ to $C_{20}$ with benzene according to claim 1, wherein the optimal pressure for carrying out the transalkylation reaction is comprised between 10-50 kgf/cm$^2$.

8. A method for obtaining mono alkyl benzene compounds with an alkyl chain having a size of $C_{10}$ to $C_{20}$ by means of the catalytic transalkylation of dialkyl benzene compounds the alkyl chains of which have a size of $C_{10}$ to $C_{20}$ with benzene according to claim 1, wherein the optimal liquid hourly space velocity (LHSV) is comprised between 0.5-5 h$^{-1}$.

* * * * *